United States Patent
Gold et al.

(10) Patent No.: US 9,989,495 B2
(45) Date of Patent: Jun. 5, 2018

(54) ACOUSTIC MONITORING METHOD FOR ADDITIVE MANUFACTURING PROCESSES

(71) Applicant: General Electric Company, Schenectady, NY (US)

(72) Inventors: Scott Alan Gold, Waynesville, OH (US); Thomas Graham Spears, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 259 days.

(21) Appl. No.: 14/946,401

(22) Filed: Nov. 19, 2015

(65) Prior Publication Data

US 2017/0146488 A1    May 25, 2017

(51) Int. Cl.
*G01N 29/24*    (2006.01)
*G01N 29/02*    (2006.01)

(52) U.S. Cl.
CPC ......... *G01N 29/02* (2013.01); *G01N 29/2418* (2013.01); *G01N 2291/267* (2013.01)

(58) Field of Classification Search
CPC ............... G01N 29/02; G01N 29/2418; G01N 2291/267
USPC .......................................................... 73/645
See application file for complete search history.

(56) References Cited

U.S. PATENT DOCUMENTS

| | | | |
|---|---|---|---|
| 4,144,766 A | 3/1979 | Wehrmeister | |
| 4,419,562 A | 12/1983 | Jon et al. | |
| 4,644,127 A | 2/1987 | La Rocca | |
| 5,065,630 A | 11/1991 | Hadcock et al. | |
| 5,445,027 A | 8/1995 | Zorner | |
| 5,487,733 A | 1/1996 | Caizza et al. | |
| 5,952,576 A | 9/1999 | Schwarz | |
| 6,078,397 A | 6/2000 | Monchalin et al. | |
| 6,554,921 B2 * | 4/2003 | Sokol | C21D 10/005 148/508 |
| 6,628,404 B1 | 9/2003 | Kelley et al. | |
| 6,732,587 B2 | 5/2004 | Lorraine et al. | |
| 6,925,346 B1 | 8/2005 | Mazumder et al. | |
| 6,940,037 B1 | 9/2005 | Kovacevic et al. | |
| 7,010,982 B2 | 3/2006 | Bergman | |
| 7,057,176 B2 | 6/2006 | Rothenfusser et al. | |

(Continued)

FOREIGN PATENT DOCUMENTS

| | | |
|---|---|---|
| AU | 623417 | 5/1992 |
| GB | 2508335 | 6/2014 |

(Continued)

OTHER PUBLICATIONS

Sensors Fusion Data from the Optic and acoustic emissions of electric ard in the GMAW-S process for welding quality assessment, Alfaro et al., May 25, 2012.*

(Continued)

*Primary Examiner* — J M Saint Surin
(74) *Attorney, Agent, or Firm* — General Electric Company; Brian P. Overbeck (57) ABSTRACT

A method of monitoring an additive manufacturing process in which a directed energy source is used to create a weld pool at an exposed build surface of a mass of powdered material, and selectively fuse the powdered material to form a workpiece, the method including measuring acoustic energy generated by the weld pool to generate a measured acoustic profile.

17 Claims, 5 Drawing Sheets

(56) References Cited

U.S. PATENT DOCUMENTS

| | | | |
|---|---|---|---|
| 7,387,027 B2* | 6/2008 | Choi | G01H 17/00 356/502 |
| 7,816,622 B2* | 10/2010 | Deaton, Jr. | B23K 26/0069 219/121.6 |
| 7,821,645 B2* | 10/2010 | Sano | G01N 29/2418 356/502 |
| 8,181,523 B2 | 5/2012 | Batzinger et al. | |
| 8,210,045 B2 | 7/2012 | Caron | |
| 8,303,886 B2 | 11/2012 | Philippi | |
| 8,497,986 B2 | 7/2013 | Ochiai et al. | |
| 8,778,255 B2 | 7/2014 | Banberg et al. | |
| 9,052,273 B2 | 6/2015 | Michaut | |
| 9,056,368 B2 | 6/2015 | Stork Genannt Wersborg | |
| 2006/0076321 A1* | 4/2006 | Maev | B23K 11/252 219/109 |
| 2007/0176312 A1 | 8/2007 | Clark et al. | |
| 2009/0206065 A1 | 8/2009 | Kruth et al. | |
| 2014/0060188 A1 | 3/2014 | Singh et al. | |
| 2014/0144895 A1 | 5/2014 | Stork Gennannt Wersborg et al. | |
| 2014/0356078 A1 | 12/2014 | Stanowski et al. | |
| 2015/0064047 A1 | 3/2015 | Hyde et al. | |
| 2015/0104802 A1 | 4/2015 | Reep et al. | |
| 2015/0177158 A1 | 6/2015 | Cheverton | |

FOREIGN PATENT DOCUMENTS

| | | | |
|---|---|---|---|
| RU | 2010142339 | * | 4/2012 |
| WO | 2016/198885 A1 | | 12/2016 |

OTHER PUBLICATIONS

Weld pool surface depth measurement using a calibrated camera and structured light, Saeed et al., 2007.*

Extended European Search Report and Opinion issued in connection with corresponding EP Application No. 6199371.2 dated Apr. 12, 2017.

* cited by examiner

ACOUSTIC MONITORING METHOD FOR ADDITIVE MANUFACTURING PROCESSES

BACKGROUND OF THE INVENTION

This invention relates generally to additive manufacturing, and more particularly to apparatus and methods for monitoring and process control in additive manufacturing.

Additive manufacturing is a process in which material is built up layer-by-layer to form a component. Unlike casting processes, additive manufacturing is limited by the position resolution of the machine and not limited by requirements for providing draft angles, avoiding overhangs, etc. Additive manufacturing is also referred to by terms such as "layered manufacturing," "reverse machining," "direct metal laser melting" (DMLM), and "3-D printing." Such terms are treated as synonyms for purposes of the present invention.

One problem with prior art additive manufacturing processes is that they typically require a post-build inspection process, such as computerized tomography ("CT"), to verify the integrity of the build. While effective, this process adds undesirable extra time and cost.

BRIEF DESCRIPTION OF THE INVENTION

This problem is addressed by a method of acoustic monitoring.

According to one aspect of the technology described herein, a method is provided for monitoring an additive manufacturing process in which a directed energy source is used to create a weld pool at an exposed build surface of a mass of powdered material, and selectively fuse the powdered material to form a workpiece. The method includes measuring acoustic energy generated by the weld pool to generate a measured acoustic profile.

According to another aspect of the technology described herein, a method of making a workpiece: includes depositing a powdered material so as to define a build surface; directing a build beam from a directed energy source to create a weld pool in the build surface, and selectively fuse the powdered material in a pattern corresponding to a cross-sectional layer of the workpiece; and measuring acoustic energy generated by the weld pool to generate a measured acoustic profile.

BRIEF DESCRIPTION OF THE DRAWINGS

The invention may be best understood by reference to the following description taken in conjunction with the accompanying drawing figures in which.

DETAILED DESCRIPTION OF THE INVENTION

Figure 1:
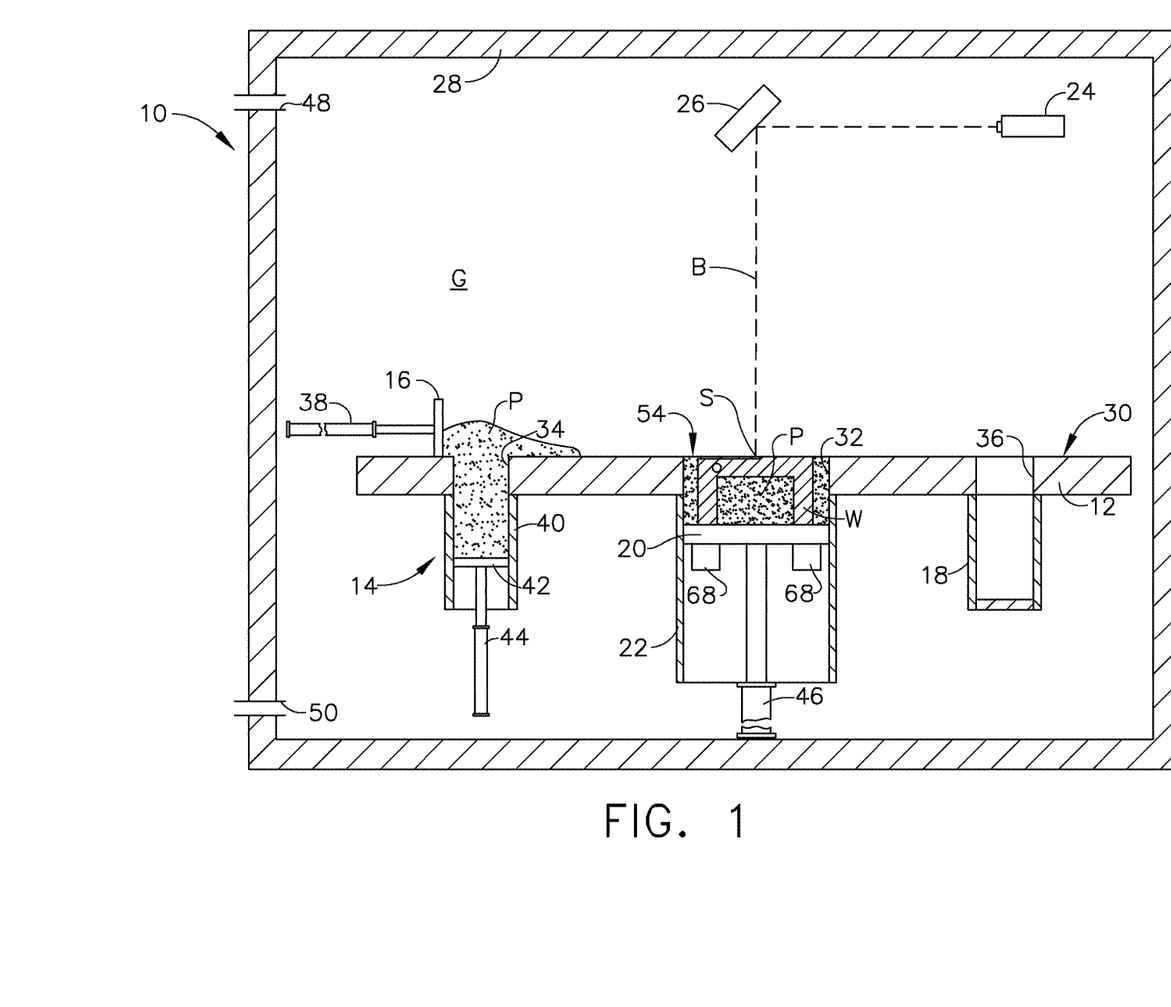
FIG. 1 is a schematic cross-sectional view of an exemplary additive manufacturing apparatus.

Referring to the drawings wherein identical reference numerals denote the same elements throughout the various views, FIG. 1 illustrates schematically an apparatus 10 for carrying out an additive manufacturing method. The basic components are a table 12, a powder supply 14, a scraper or recoater 16, an overflow container 18, a build platform 20 surrounded by a build chamber 22, a directed energy source 24, and a beam steering apparatus 26, all surrounded by an enclosure 28. Each of these components will be described in more detail below.

The table 12 is a rigid structure defining a planar worksurface 30. The worksurface 30 is coplanar with and defines a virtual workplane. In the illustrated example it includes a build opening 32 communicating with the build chamber 22 and exposing the build platform 20, a supply opening 34 communicating with the powder supply 14, and an overflow opening 36 communicating with the overflow container 18.

The recoater 16 is a rigid, laterally-elongated structure that lies on the worksurface 30. It is connected to an actuator 38 operable to selectively move the recoater 16 along the worksurface 30. The actuator 38 is depicted schematically in FIG. 1, with the understanding devices such as pneumatic or hydraulic cylinders, ballscrew or linear electric actuators, and so forth, may be used for this purpose.

The powder supply 14 comprises a supply container 40 underlying and communicating with the supply opening 34, and an elevator 42. The elevator 42 is a plate-like structure that is vertically slidable within the supply container 40. It is connected to an actuator 44 operable to selectively move the elevator 42 up or down. The actuator 44 is depicted schematically in FIG. 1, with the understanding that devices such as pneumatic or hydraulic cylinders, ballscrew or linear electric actuators, and so forth, may be used for this purpose. When the elevator 42 is lowered, a supply of powder "P" of a desired composition (for example, metallic, ceramic, and/or organic powder) may be loaded into the supply container 40. When the elevator 42 is raised, it exposes the powder P above the worksurface 30. It should be appreciated that other suitable forms and/or types of powder supply 14 may be used. For example, the powder supply 14 may be positioned above the worksurface 30 and include a powder container that drops powder onto the worksurface 30 at a pre-determined flow rate.

The build platform 20 is a plate-like structure that is vertically slidable below the build opening 32. It is connected to an actuator 46 operable to selectively move the build platform 20 up or down. The actuator 46 is depicted schematically in FIG. 1, with the understanding that devices such as pneumatic or hydraulic cylinders, ballscrew or linear electric actuators, and so forth, may be used for this purpose. When the build platform 20 is lowered into the build chamber 22 during a build process, the build chamber 22 and the build platform 20 collectively surround and support a mass of powder P along with any components being built. This mass of powder is generally referred to as a "powder bed", and this specific category of additive manufacturing process may be referred to as a "powder bed process".

The overflow container 18 underlies and communicates with the overflow opening 36, and serves as a repository for excess powder P.

The directed energy source 24 may comprise any known device operable to generate a beam of suitable power and other operating characteristics to melt and fuse the metallic powder during the build process, described in more detail below. For example, the directed energy source 24 may be a laser. Other directed-energy sources such as electron beam guns are suitable alternatives to a laser.

The beam steering apparatus 26 may include one or more mirrors, prisms, lenses and/or electromagnets and provided with suitable actuators, and arranged so that a beam "B" from the directed energy source 24 can be focused to a desired spot size and steered to a desired position in plane coincident with the worksurface 30. For purposes of convenient description, this plane may be referred to as an X-Y plane, and a direction perpendicular to the X-Y plane is denoted as a Z-direction (X, Y, and Z being three mutually perpendicular directions). The beam B may be referred to herein as a "build beam".

The enclosure 28 serves to isolate and protect the other components of the apparatus 10. It may be provided with a flow of an appropriate shielding gas "G", for example nitrogen, argon, or other gases or gas mixtures. The gas G may be provided as a static pressurized volume or as a dynamic flow. The enclosure 28 may be provided with inlet and outlet ports 48, 50 respectively for this purpose.

The basic build process for a workpiece W using the apparatus described above is as follows. The build platform 20 is moved to an initial high position. The build platform 20 is lowered below the worksurface 30 by a selected layer increment. The layer increment affects the speed of the additive manufacturing process and the resolution of the workpiece W. As an example, the layer increment may be about 10 to 50 micrometers (0.0003 to 0.002 in.). Powder "P" is then deposited over the build platform 20, for example, the elevator 42 of the supply container 40 may be raised to push powder through the supply opening 34, exposing it above the worksurface 30. The recoater 16 is moved across the worksurface to spread the raised powder P horizontally over the build platform 20. Any excess powder P drops through the overflow opening 36 into the overflow container 18 as the recoater 16 passes from left to right. Subsequently, the recoater 16 may be moved back to a starting position. The leveled powder P may be referred to as a "build layer" 52 and the exposed upper surface thereof may be referred to as a "build surface" 54 (see FIG. 2).

The directed energy source 24 is used to melt a two-dimensional cross-section or layer of the workpiece W being built. The directed energy source 24 emits a beam "B" and the beam steering apparatus 26 is used to steer the focal spot "S" of the build beam B over the exposed powder surface in an appropriate pattern. A small portion of exposed layer of the powder P surrounding the focal spot S, referred to herein as a "weld pool" 56 (best seen in FIG. 2) is heated by the build beam B to a temperature allowing it to melt, flow, and consolidate. As an example, the weld pool 56 may be on the order of 100 micrometers (0.004 in.) wide. This step may be referred to as fusing the powder P.

The build platform 20 is moved vertically downward by the layer increment, and another layer of powder P is applied in a similar thickness. The directed energy source 24 again emits a build beam B and the beam steering apparatus 26 is used to steer the focal spot S of the build beam B over the exposed powder surface in an appropriate pattern. The exposed layer of the powder P is heated by the build beam B to a temperature allowing it to melt, flow, and consolidate both within the top layer and with the lower, previously-solidified layer, again maintaining the crystallographic orientation of the layers below.

This cycle of moving the build platform 20, applying powder P, and then directed energy melting the powder P is repeated until the entire workpiece W is complete.

Figure 2:
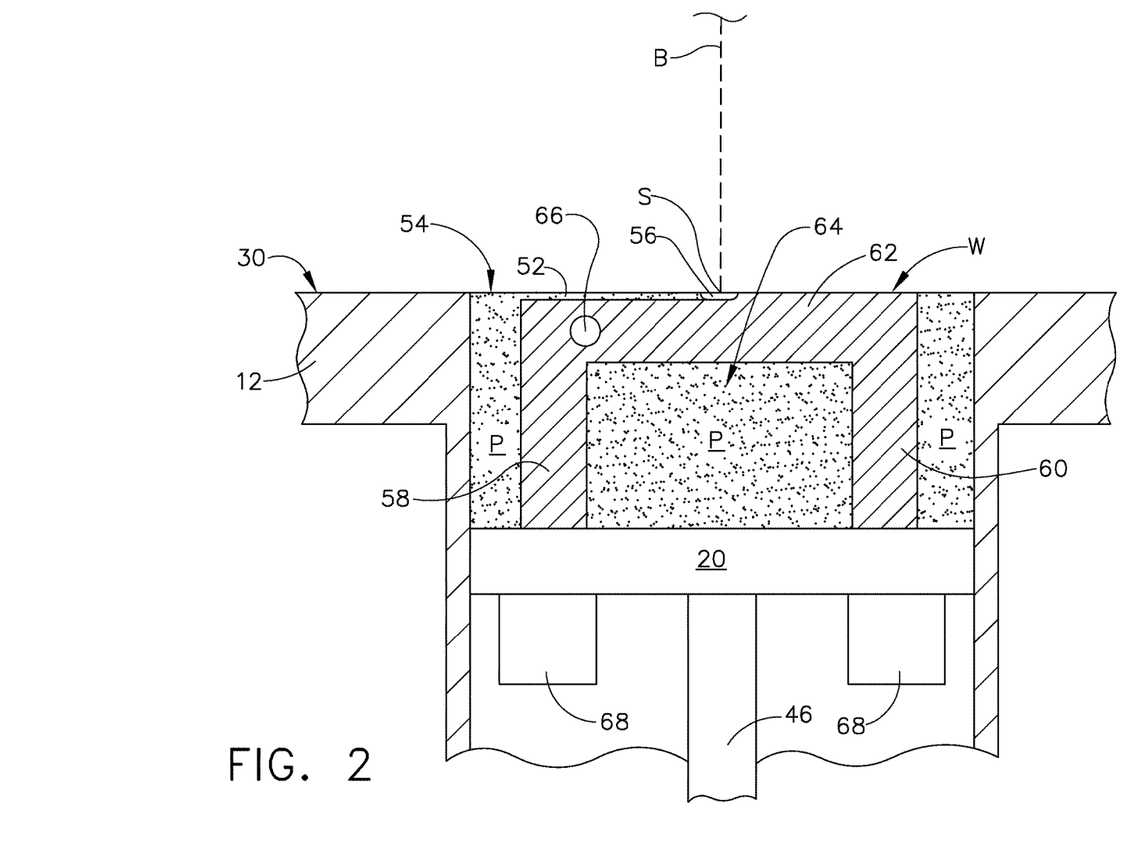
FIG. 2 is an enlarged view of a portion of FIG. 1.

FIG. 2 shows in more detail a workpiece W being constructed in a powder bed of the type described above. The exemplary workpiece W includes a pair of spaced-apart vertical walls 58, 60 interconnected by horizontal wall 62. A cavity 64 is present between the vertical walls 58, 60 and is filled with powder P; additional powder P is present between the vertical walls 58, 60 and the side walls of the build chamber 22.

Figure 3:
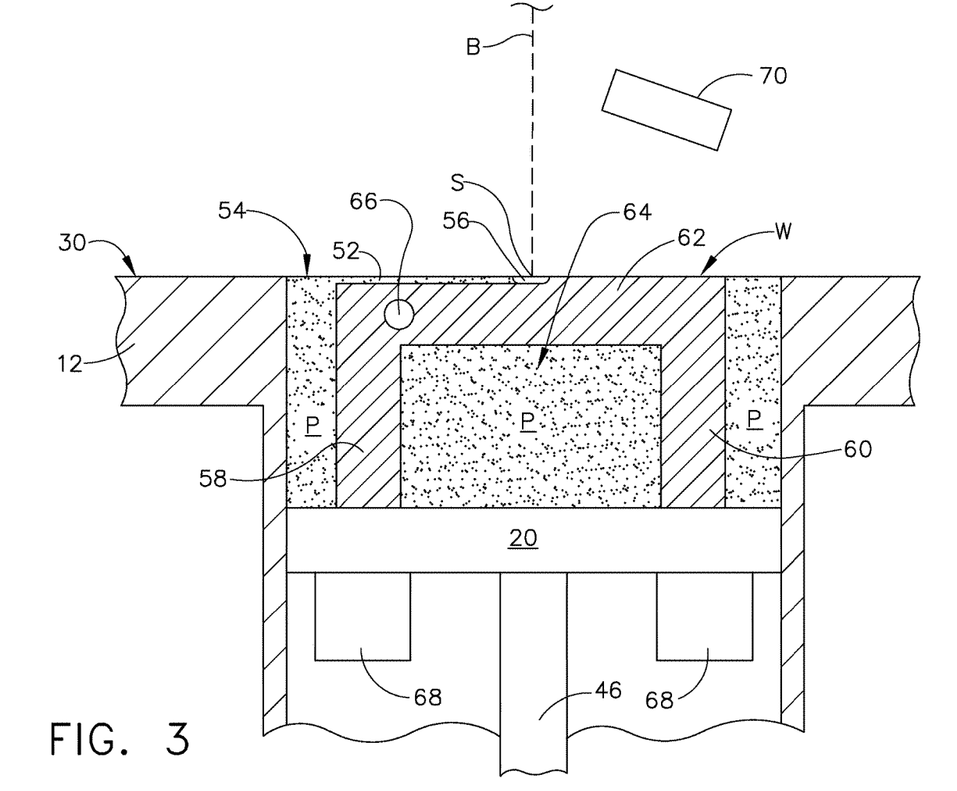
FIG. 3 is an enlarged cross-sectional view of an alternative additive manufacturing apparatus.

An acoustic inspection process may be incorporated into the build process described above. Generally stated, the acoustic monitoring process includes using an acoustic sensor 68 to measure acoustic signals during the build process and monitoring those signals for irregularities indicative of a defect in the workpiece W. The sensor 68 may be mounted in any location within the apparatus 10 where it can receive acoustic signals generated by the additive build process. For example, FIG. 2 illustrates contact microphones 68 mounted to the underside of the build platform 20. FIG. 3 illustrates a free air microphone 70 disposed above the table 12. In general, this type of process may be referred to as "acoustic monitoring". As used herein, the term "acoustic" refers generally to the transmission of energy through a medium such as a gas or a solid, without regard to the frequency range of such energy.

During the fusing step described above, the action of the build beam B in generating the weld pool 56 inherently generates an acoustic wave radiating out from the weld pool 56. This acoustic wave travels through the structure of the table 12 and the gas G within the enclosure 28, and can be detected by the microphones 68, 70 described above in order to generate a measured acoustic profile. It should be appreciated that the acoustic profile may be recorded at any suitable pre-determined interval of layer increments.

If the workpiece W is properly formed, then the fusing process is smooth and very little variation occurs in the amount of acoustic energy being induced by the fusing process. However, if the workpiece W experiences a defect such as a crack or void, it will cause a change in the nature of the acoustic signal propagating through the apparatus 10.

Figure 4:
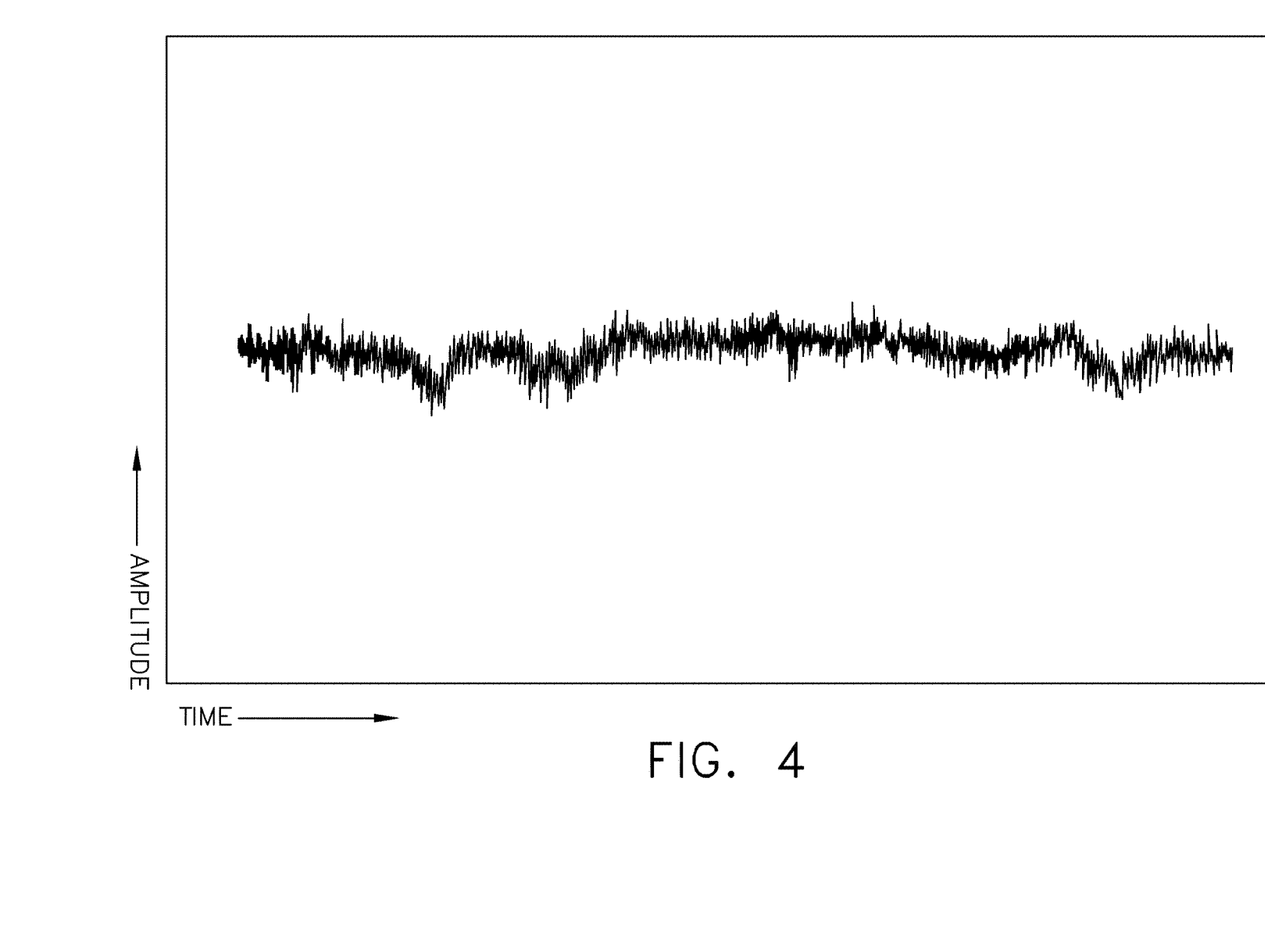
FIG. 4 is a baseline acoustic profile of a "known good" workpiece build process.

The acoustic monitoring process uses a "known good" workpiece acoustic profile as a comparison to provide acoustic signal analysis. The comparison may be conducted after the build process is complete, as a means of inspection and quality control. Alternatively, the comparison may take place in real time. For each specific build (different sized and shaped workpieces) a new signal profile can be developed for comparison. Thus, a baseline signal profile may be developed for each increment layer of the build. This is done so that variations in acoustics due to a specific profile of a workpiece, as opposed to a defect, is taken into account. A non-limiting example of a known good signal profile, showing acoustic amplitude versus time, is shown in FIG. 4.

Figure 5:
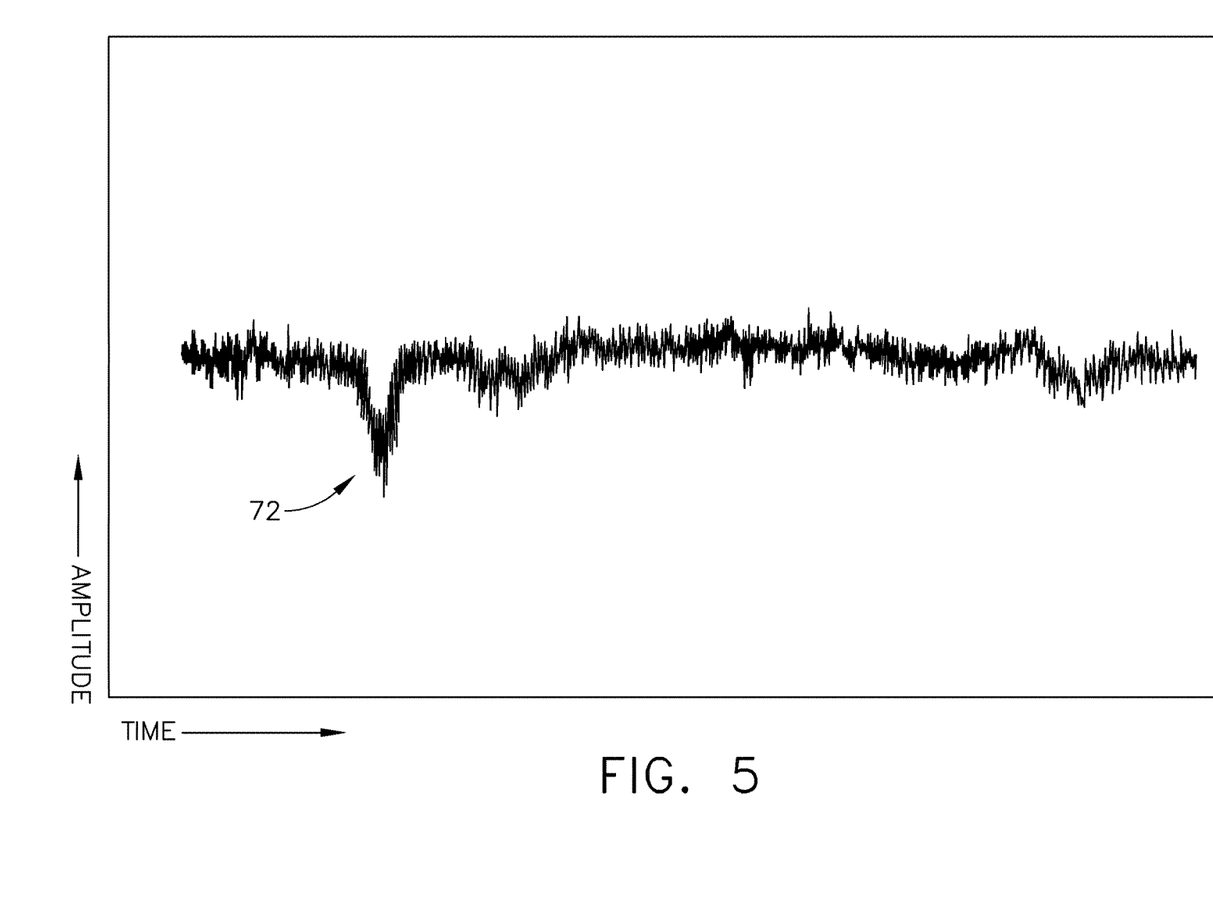
FIG. 5 is an acoustic profile showing a large defect in a workpiece during a build process.

A non-limiting example of a measured acoustic profile, showing amplitude versus time, is shown in FIG. 5. As illustrated, a small dip or dropout 72 present in the measured acoustic profile that is not present in the baseline acoustic profile shown in FIG. 4 indicates that a defect is present.

During the build process and while the acoustic profile is being measured, the position in space of the weld pool 56 may also be tracked. For example, the X-Y position of the weld pool 56 is known at all times based on the steering commands fed to the beam steering apparatus 26. The Z position of the weld pool 56 is known based on the position of the build platform 20. The weld pool position may be tracked in synchronization with the acoustic profile, so that for any point in time, the positional origin of the acoustic signal being tracked is known.

In addition to or as an alternative to tracking the position of the weld pool 56 as described above, the microphones 68, 70 may be used to localize the source of acoustic energy. For example, if multiple microphones 68, 70 are positioned at known, space-apart locations, a process of triangulation or trilateralization may be used to calculate the position of the acoustic energy source. This positional information may be tracked in synchronization with the acoustic profile.

The availability of synchronized positional information allows defects to be localized within the workpiece W. This information may prove invaluable when attempting to locate defects in a completed workpiece W, and/or when attempting to rework defects that occur during the build process.

The acoustic monitoring method described above may be implemented for various purposes in an additive manufacturing process. For example, an inspection could be made during the fusing of each build layer 52, or immediately after each build layer 52 is complete, or after several build layers 52 have been completed. This allows confirmation that each layer or group of layers has been built correctly and is free of defects.

If a workpiece is discovered to have a defect, the build process could be abandoned. Alternatively, if a defect is discovered, the apparatus 10 could be used to repair the defect, by directing the build beam B to the workpiece W over the defect, creating a weld pool which remelts the material and permits it to flow into and fill the defect.

The monitoring process described above may be used to provide real-time feedback which can be used to modify the additive build process. For example, if the inspection process determines that the build is creating defects, one or more process parameters such as laser power, scanning speed, gas flow, etc. may be changed to restore performance to nominal or eliminate the source of defects.

The monitoring process described above may also be used as part of a plan of statistical process control. In particular, the inspection process could be used to identify sources of variation in the process. Process parameters could then be altered in subsequent builds to reduce or eliminate sources of variation.

The monitoring process described above may also be used as part of a plan of quality control documentation. In particular, the acoustic profile generated during a build may be stored for later reference. Furthermore, the stored acoustic profile may be used to validate that the build procedure of an individual workpiece W conforms to a predetermined standard. The process described herein allows mapping the thickness of overhanging layers in an additive structure, and detection of variations from nominal with high precision. This has the potential to eliminate post-build quality control processes such as CT scanning currently used in the prior art.

The foregoing has described a method for acoustic monitoring of an additive manufacturing process. All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends any novel one, or any novel combination, of the features disclosed in this specification (including any accompanying potential points of novelty, abstract and drawings), or to any novel one, or any novel combination, of the steps of any method or process so disclosed.

What is claimed is:

1. A method of monitoring an additive manufacturing process in which a directed energy source is used to create a weld pool at an exposed build surface of a mass of powdered material, and selectively fuse the powdered material to form a workpiece, the method comprising:
   measuring acoustic energy generated by the weld pool to generate a measured acoustic profile; and
   controlling at least one aspect of the additive manufacturing process in response to the measured acoustic profile,
   wherein the step of controlling includes taking a discrete action in response to the acoustic signal profile deviating from a baseline acoustic profile.

2. The method of claim 1 further comprising comparing the measured acoustic profile to the baseline acoustic profile.

3. The method of claim 2 wherein the baseline acoustic profile is representative of a known good workpiece.

4. The method of claim 2 wherein a difference between the measured acoustic profile and the baseline acoustic profile indicates the presence of a defect in the workpiece.

5. The method of claim 1 further comprising monitoring a position of the weld pool while measuring the acoustic signal.

6. The method of claim 5 wherein the position of weld pool is monitored by two or more spaced-apart acoustic sensors positioned at known locations relative to the mass of powdered material.

7. The method of claim 1 further comprising storing a record of the measured acoustic profile.

8. The method of claim 1 wherein the discrete action is stopping the additive manufacturing process.

9. A method of making a workpiece, comprising:
   depositing a powdered material so as to define a build surface;
   directing a build beam from a directed energy source to create a weld pool in the build surface, and selectively fuse the powdered material in a pattern corresponding to a cross-sectional layer of the workpiece;
   measuring acoustic energy generated by the weld pool to generate a measured acoustic profile; and
   controlling at least one aspect of the method of making the workpiece in response to the measured acoustic profile,
   wherein the step of controlling includes taking a discrete action in response to the acoustic signal profile deviating from a baseline acoustic profile.

10. The method of claim 9 further comprising comparing the measured acoustic profile to the baseline acoustic profile.

11. The method of claim 10 wherein the baseline acoustic profile is representative of a known good workpiece.

12. The method of claim 10 wherein a difference between the measured acoustic profile and the baseline acoustic profile indicates the presence of a defect in the workpiece.

13. The method of claim 12 further comprising repairing the defect by using the directed energy source to create a weld pool over the defect, permitting previously-fused material to flow into and fill the defect.

14. The method of claim 9 further comprising monitoring a position of the weld pool while measuring the acoustic signal.

15. The method of claim 14 wherein the position of the weld pool is monitored by two or more spaced-apart acoustic sensors positioned at known locations relative to the mass of powdered material.

16. The method of claim 9 further comprising storing a record of the measured acoustic profile.

17. The method of claim 9 wherein the discrete action is stopping the additive manufacturing process.

* * * * *